(12) United States Patent
Candau

(10) Patent No.: US 7,368,105 B2
(45) Date of Patent: May 6, 2008

(54) PHOTOSTABILIZATION OF DIBENZOYLMETHANE UV-SCREENING AGENTS WITH ARYLALKYL BENZOATE/BIS-RESORCINYL TRIAZINE COMPOUNDS AND PHOTOPROTECTIVE COMPOSITIONS COMPRISED THEREOF

(75) Inventor: Didier Candau, Bievres (FR)

(73) Assignee: L'Oreal, Paris (FR)

( * ) Notice: Subject to any disclaimer, the term of this patent is extended or adjusted under 35 U.S.C. 154(b) by 323 days.

(21) Appl. No.: 11/172,932

(22) Filed: Jul. 5, 2005

(65) Prior Publication Data

US 2006/0008429 A1    Jan. 12, 2006

Related U.S. Application Data

(60) Provisional application No. 60/589,009, filed on Jul. 20, 2004.

(30) Foreign Application Priority Data

Jul. 2, 2004    (FR)    .................. 04 51419

(51) Int. Cl.
| | |
|---|---|
| *A61Q 17/04* | (2006.01) |
| *A61Q 17/00* | (2006.01) |
| *A61Q 19/04* | (2006.01) |
| *A61Q 19/00* | (2006.01) |
| *A61K 8/02* | (2006.01) |

(52) U.S. Cl. .................... 424/59; 424/60; 424/400; 424/401

(58) Field of Classification Search ................ 424/59, 424/60, 400, 401
See application file for complete search history.

(56) References Cited

U.S. PATENT DOCUMENTS

| | | | |
|---|---|---|---|
| 5,882,633 A | 3/1999 | Pisson et al. |
| 6,103,221 A | 8/2000 | Arnaud et al. |
| 6,509,008 B1 | 1/2003 | Candau |
| 7,132,097 B2 | 11/2006 | Bertz et al. |
| 7,166,275 B2 | 1/2007 | Bertz et al. |
| 2003/0185770 A1 | 10/2003 | Birrenbach |
| 2005/0152858 A1 | 7/2005 | Bertz et al. |
| 2005/0281763 A1 | 12/2005 | Suginaka et al. |
| 2005/0288205 A1 | 12/2005 | Walele et al. |
| 2006/0067900 A1 | 3/2006 | Bertz et al. |
| 2006/0067901 A1 | 3/2006 | Bertz et al. |

FOREIGN PATENT DOCUMENTS

| | | |
|---|---|---|
| FR | 2783712 A1 | 3/2000 |
| FR | 2 800 991 A1 | 5/2001 |
| JP | 2000-136110 A | 5/2000 |
| JP | 2002-226350 A | 8/2002 |
| JP | 2003-532665 A | 11/2003 |
| WO | WO 02/17873 A1 | 3/2002 |
| WO | WO 03/039510 A1 | 5/2003 |
| WO | WO 2005/009341 A2 | 2/2005 |
| WO | WO 2005/069822 A2 | 8/2005 |
| WO | 2005/117823 A1 | 12/2005 |
| WO | 2005/117824 A1 | 12/2005 |
| WO | 2005/117825 A1 | 12/2005 |
| WO | 2006/009828 A1 | 1/2006 |
| WO | WO 2006/041506 A2 | 4/2006 |

OTHER PUBLICATIONS

Japanese Official Action dated Feb. 27, 2007 comments and Notice of Reasons for Rejection.
XP 002320817, "X-Tend™ 226, A Novel Ester with High Solubilizing Capacity", International Specialty Products, Aug. 2003.
Chatelain et al., "Photostabilization of Butyl Methoxydibenzoylmethane (Avobenzone) and Ethylhexyl Methoxycinnamate by Bis-ethyihexyloxyphenol Methoxydyphenyl Triazine (Tinosorb S), a New UV Broadband Filter", Photochemistry and Photobiology, Sep. 2001, pp. 401-406, vol. 74, No. 3, Oxford, GB.
French Search Report corresponding to FR 04/51419, issued on Mar. 14, 2005, 2 pages.
English translation of French Search Report for FR 04/51419.

*Primary Examiner*—Shelley A. Dodson
(74) *Attorney, Agent, or Firm*—Buchanan, Ingersoll & Rooney, PC

(57) ABSTRACT

Topically applicable, photostable compositions with respect to UV radiation contain at least one dibenzoylmethane UV-screening agent and at least one arylalkyl benzoate compound and at least one bis-resorcinyl triazine compound.

21 Claims, No Drawings

PHOTOSTABILIZATION OF DIBENZOYLMETHANE UV-SCREENING AGENTS WITH ARYLALKYL BENZOATE/BIS-RESORCINYL TRIAZINE COMPOUNDS AND PHOTOPROTECTIVE COMPOSITIONS COMPRISED THEREOF

CROSS-REFERENCE TO PRIORITY/PROVISIONAL APPLICATIONS

This application claims priority under 35 U.S.C. § 119(a)-(d) of FR 04/51419, filed Jul. 2, 2004, and claims benefit under 35 U.S.C. § 119(e) of provisional application Ser. No. 60/589,009, filed Jul. 20, 2004, each hereby expressly incorporated by reference and each assigned to the assignee hereof.

CROSS-REFERENCE TO COMPANION APPLICATIONS

Applications Ser. No. 11/172,902 and Ser. No. 11/172,949, each filed concurrently herewith and each also assigned to the assignee hereof.

BACKGROUND OF THE INVENTION

1. Technical Field of the Invention

The present invention relates to a process for photostabilizing, with respect to UV radiation, at least one dibenzoylmethane UV-screening agent with at least one arylalkyl benzoate compound and at least one bis-resorcinyl triazine compound.

The present invention also relates to novel UV-photoprotective compositions, in particular cosmetic compositions for topical application.

2. Description of Background and/or Related and/or Prior Art

It is known that light radiation with wavelengths of from 280 nm to 400 nm permits tanning of the human epidermis and that light rays with wavelengths more particularly of from 280 to 320 nm, known as UV-B rays, cause skin burns and erythema which can harm the development of a natural tan. For these reasons, as well as for aesthetic reasons, there is a constant demand for means of controlling this natural tanning in order thus to control the color of the skin; this UV-B radiation should thus be screened out.

It is also known that UV-A rays, with wavelengths of from 320 to 400 nm, which cause tanning of the skin, are liable to induce adverse changes therein, in particular in the case of sensitive skin or skin which is continually exposed to solar radiation. UV-A rays cause in particular a loss of elasticity of the skin and the appearance of wrinkles leading to premature aging of the skin. They promote triggering of the erythemal reaction or amplify this reaction in certain individuals and may even be the cause of phototoxic or photoallergic reactions. Thus, for aesthetic and cosmetic reasons such as the conservation of the skin's natural elasticity, for example, an increasingly large number of individuals wish to control the effect of UV-A rays on their skin. It is thus desirable also to screen out UV-A radiation.

For the purpose of protecting the skin and keratin materials against UV radiation, antisun compositions comprising organic screening agents that are active in the UV-A range and in the UV-B range are generally used. The majority of these screening agents are liposoluble.

In this respect, one particularly advantageous family of UV-A screening agents currently consists of dibenzoylmethane derivatives, and in particular 4-tert-butyl-4'-methoxydibenzoylmethane, which have high intrinsic absorbing power. These dibenzoylmethane derivatives, which are products which are now well known per se as screening agents that are active in the UV-A range, are described in particular in FR-A-2,326,405 and FR-A-2,440,933, as well as in EP-A-0,114,607; 4-tert-butyl-4'-methoxydibenzoylmethane is moreover currently marketed under the trademark "Parsol 1789" by Roche Vitamins.

Unfortunately, it has been found that dibenzoylmethane derivatives are products that are relatively sensitive to ultraviolet radiation (especially UV-A), i.e., more specifically, they have an annoying tendency to be degraded more or less quickly under the action of this UV. Thus, this substantial lack of photochemical stability of dibenzoylmethane derivatives towards ultraviolet radiation, to which they are by nature intended to be subjected, does not make it possible to ensure constant protection during prolonged exposure to the sun, and so the user must make repeated applications at regular and close time intervals in order to obtain effective protection of the skin against UV rays.

Dibenzoylmethane derivatives are oil-soluble solid screening agents. Among the oils capable of effectively dissolving these UV-screening agents, alkyl benzoates are known, especially C12/C15 alkyl benzoates, for instance the commercial products Finsolv TN or Witconol APM manufactured and marketed by Witco.

However, the alkyl benzoates known hitherto do not solve the problem of the photostability of dibenzoylmethane derivatives with respect to UV radiation.

SUMMARY OF THE INVENTION

It has now surprisingly been determined that by combining the dibenzoylmethane UV-screening agents mentioned above with an effective amount of an arylalkyl benzoate compound and a bis-resorcinyl triazine compound, it is possible to improve the photochemical stability (or photostability) of these same dibenzoylmethane derivatives, in a substantial and noteworthy manner.

This essential discovery forms the basis of the present invention.

Thus, the present invention features a process for improving the stability of at least one dibenzoylmethane UV-screening agent with respect to UV radiation, which comprises combining said at least one dibenzoylmethane derivative with at least one arylalkyl benzoate compound and at least one bis-resorcinyl triazine compound.

This invention also features cosmetic or dermatological compositions for topical application, comprising, formulated into a cosmetically acceptable support:

(a) at least one UV-screening agent of the dibenzoylmethane derivative type, (b) at least one arylalkyl benzoate compound, and (c) at least one bis-resorcinyl triazine compound.

Too, the present invention also features formulating an arylalkyl benzoate compound into a cosmetic or dermatological composition comprising at least one dibenzoylmethane UV-screening agent, for the purpose of improving the stability with respect to UV rays of the said at least one dibenzoylmethane derivative.

Other characteristics, aspects and advantages of the invention will become apparent from the detailed description that follows.

DETAILED DESCRIPTION OF BEST MODE AND SPECIFIC/PREFERRED EMBODIMENTS OF THE INVENTION

Among the dibenzoylmethane compounds that are especially representative according to the invention are:

2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylmethane;
4,4'-dimethoxydibenzoylmethane;
4-tert-butyl-4'-methoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane; and
2,6-dimethyl-4-tert-butyl-4'-methoxydibenzoylmethane.

Among the dibenzoylmethane derivatives mentioned above, 4-isopropyldibenzoylmethane will be used in particular, which is marketed under the name "Eusolex 8020" by Merck, and corresponds to the following formula:

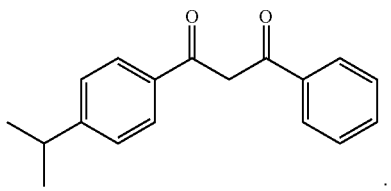

It is most particularly preferred to use 4-(tert-butyl)-4'-methoxydibenzoylmethane or Butyl Methoxy Dibenzoylmethane, marketed under the trademark "Parsol 1789" by Roche Vitamins; this screening agent corresponds to the following formula:

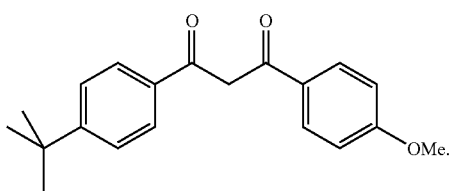

The dibenzoylmethane derivative(s) may be present in the compositions in accordance with the invention in contents preferably ranging from 0.01% to 10% by weight and more preferably from 0.1% to 6% by weight relative to the total weight of the composition.

The arylalkyl benzoate compounds in accordance with the invention are preferably selected from among those of formula (I) or (II) below:

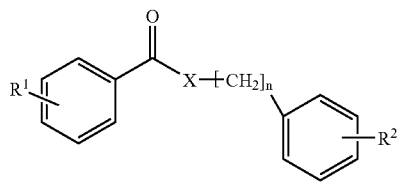

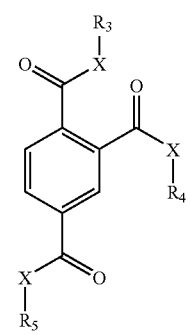

in which:
X is O, S or N;
n is an integer ranging from 1 to 10 and more preferably from 2 to 6;
$R^1$ and $R^2$, which may be identical or different, are each a hydrogen atom, a hydroxyl group, a linear or branched $C_1$-$C_4$ alkoxy radical (preferably methoxy or ethoxy), a nitro radical, an amino radical, or a $C_6H_6SO_2$ radical;
$R^3$, $R^4$ and $R^5$, which may be identical or different, are each a radical of formula:

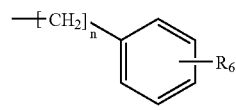

in which n has the same definition indicated above; and $R_6$ is a hydrogen atom, a hydroxyl group, a linear or branched $C_1$-$C_4$ alkoxy radical (preferably methoxy or ethoxy), a nitro radical, an amino radical, or a $C_6H_6SO_2$ radical.

The arylalkyl benzoate compounds in accordance with the invention and the syntheses thereof have been known for a long time in the chemistry literature and especially in PL-55230.

Among the arylalkyl benzoate compounds mentioned above, 2-ethyl phenyl benzoate will be used more particularly

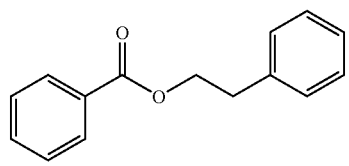

for instance the commercial product X-Tend 226® marketed by ISP.

The arylalkyl benzoate compounds in accordance with the invention may be present in the compositions in accordance with the invention in contents ranging from 0.1% to 40% by weight and more preferably from 0.1% to 30% by weight relative to the total weight of the composition.

The bis-resorcinyl triazine compounds in accordance with the present invention correspond to formula (III) below:

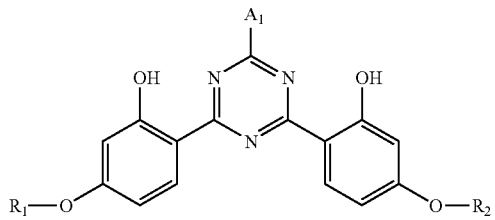
(III)

in which:
(i) the radicals $R_1$ and $R_2$, which may be identical or different, are each a $C_3$-$C_{18}$ alkyl radical, a $C_2$-$C_{18}$ alkenyl radical or a residue of formula —$CH_2$—CH(OH)—$CH_2$—$OT_1$ in which $T_1$ is a hydrogen atom or a $C_1$-$C_8$ alkyl radical;
(ii) the radicals $R_1$ and $R_2$, which may be identical or different, may also denote a residue of formula (1) below:

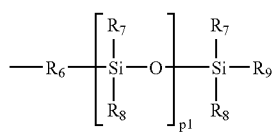
(1)

in which:
$R_6$ is a covalent bond, a linear or branched $C_1$-$C_4$ alkyl radical or a residue of formula —$C_{m1}H_{2m1}$—O— in which $m_1$ is a number ranging from 1 to 4;
$p_1$ is a number ranging from 0 to 5;
the radicals $R_7$, $R_8$ and $R_9$, which may be identical or different, are each a $C_1$-$C_{18}$ alkyl radical, a $C_1$-$C_{18}$ alkoxy radical or a residue of formula:

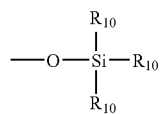
(2)

in which $R_{10}$ is a $C_1$-$C_5$ alkyl radical;
$A_1$ is a residue corresponding to one of the following formulae:

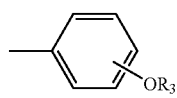
(3)

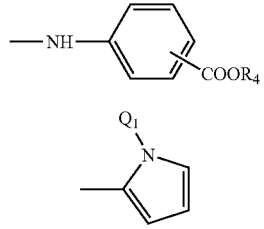
(4)

(5)

in which:
$R_3$ is a hydrogen atom, a $C_1$-$C_{10}$ alkyl radical, a radical of formula: —$(CH_2CHR_5$—O$)_{n1}R_4$ in which $n_1$ is a number ranging from 1 to 16 or a residue of structure $CH_2$—CH—(OH)—$CH_2OT_1$ with $T_1$ having the same definition indicated above,
$R_4$ is hydrogen, a metallic cation M, a $C_1$-$C_5$ alkyl radical or a residue of formula —$(CH_2)m_2$—$OT_1$ in which $m_2$ is a number ranging from 1 to 4 and $T_1$ has the same definition indicated above,
$Q_1$ is a $C_1$-$C_{18}$ alkyl radical.

In formulae (III) and (1) to (5) described above:
the alkyl radicals are linear or branched and may be selected, for example, from among methyl, ethyl, n-propyl, isopropyl, n-butyl, sec-butyl, tert-butyl, amyl, isoamyl, tert-amyl, heptyl, octyl, isooctyl, nonyl, decyl, undecyl, dodecyl, tetradecyl, pentadecyl, hexadecyl, heptadecyl or octadecyl;
the alkenyl radicals may be selected, for example, from among allyl, methallyl, isopropenyl, 2-butenyl, 3-butenyl, isobutenyl, n-penta-2,4-dienyl, 3-methylbut-2-enyl, n-oct-2-enyl, n-dodec-2-enyl, isododecenyl and n-octadec-4-enyl;
the alkoxy radicals are linear or branched and may be selected, for example, from among methoxy, ethoxy, n-propoxy, isopropoxy, n-butoxy, sec-butoxy, tert-butoxy, amyloxy, isoamyloxy and tert-amyloxy;
the $C_1$-$C_5$ monoalkylamino or dialkylamino radicals may be selected, for example, from among methylamino, ethylamino, propylamino, n-butylamino, sec-butylamino, tert-butylamino, pentylamino, dimethylamino, diethylamino, dibutylamino and methylethylamino;
the metallic cations are alkali metal, alkaline-earth metal or metallic cations selected, for example, from among lithium, potassium, sodium, calcium, magnesium, copper and zinc.

The bis-resorcinyl triazine compounds of formula (II) of the invention are screening agents that are already known per se. They are described and prepared according to the syntheses indicated in EP-A-0,775,698.

As examples of compounds of formula (II) that may be used, representative are:
2,4-bis{[4-(2-ethylhexyloxy)-2-hydroxy]phenyl}-6-(4-methoxyphenyl)-1,3,5-triazine;
2,4-bis{[4-(3-(2-propyloxy)-2-hydroxypropyloxy)-2-hydroxy]phenyl}-6-(4-methoxyphenyl)-1,3,5-triazine;
2,4-bis{[4-(2-ethylhexyloxy)-2-hydroxy]phenyl}-6-[4-(2-methoxyethylcarboxyl)phenylamino]-1,3,5-triazine;
2,4-bis{[4-tris(trimethylsiloxysilylpropyloxy)-2-hydroxy]phenyl}-6-(4-methoxyphenyl)-1,3,5-triazine;
2,4-bis{[4-(2"-methylpropenyloxy)-2-hydroxy]phenyl}-6-(4-methoxyphenyl)-1,3,5-triazine;

2,4-bis{[4-(1',1',1',3',5',5',5'-heptamethyltrisiloxy-2"-methylpropyloxy)-2-hydroxy]phenyl}-6-(4-methoxyphenyl)-1,3,5-triazine;

2,4-bis{[4-[3-(2-propyloxy)-2-hydroxypropyloxy]-2-hydroxy]phenyl}-6-[(4-ethylcarboxyl)phenylamino]-1,3,5-triazine;

2,4-bis{[4-(2-ethylhexyloxy)-2-hydroxy]phenyl}-6-(1-methylpyrrol-2-yl)-1,3,5-triazine.

The compounds derived from bis-resorcinyl triazine that are more particularly preferred according to the invention are selected from the group consisting of:

2,4-bis{[4-(2-ethylhexyloxy)-2-hydroxy]phenyl}-6-(4-methoxyphenyl)-1,3,5-triazine;

2,4-bis{[4-tris(trimethylsiloxysilylpropyloxy)-2-hydroxy]phenyl}-6-(4-methoxyphenyl)-1,3,5-triazine;

2,4-bis{[4-(1',1',1',3',5',5',5'-heptamethyltrisiloxy-2"-methylpropyloxy)-2-hydroxy]phenyl}-6-(4-methoxyphenyl)-1,3,5-triazine.

The compound 2,4-bis{[4-(2-ethylhexyloxy)-2-hydroxy]phenyl}-6-(4-methoxyphenyl)-1,3,5-triazine or Bis-Ethylhexyloxyphenol Methoxyphenyl Triazine (INCI name), such as the product marketed under the trademark "Tinosorb S" by Ciba Geigy, will be used more particularly.

The bis-resorcinyl triazine compound(s) of formula (III) is (are) generally present in the screening compositions according to the invention in a concentration ranging from 0.1% to 20% by weight, more preferably from 1% to 10% by weight and more particularly from 2% to 8% by weight relative to the total weight of the composition.

According to the present invention, the photostabilizing mixture of arylalkyl benzoate compound/bis-resorcinyl triazine will be used in a sufficient amount for obtaining an appreciable and significant improvement in the photostability of the dibenzoylmethane derivative in a given composition. This minimum amount of photostabilizer to be used may vary according to the amount of dibenzoylmethane present at the start in the composition and according to the nature of the cosmetically acceptable support adopted for the composition. It may be determined without any difficulty by means of a standard test for measuring photostability.

The compositions in accordance with the invention may also comprise other additional UV-A-active and/or UV-B-active organic or mineral photoprotective agents that are water-soluble or liposoluble or insoluble in the cosmetic solvents commonly used.

The additional organic photoprotective agents are selected especially from anthranilates; cinnamic derivatives; salicylic derivatives; camphor derivatives; benzophenone derivatives; β,β-diphenylacrylate derivatives; triazine derivatives other than those of the bis-resorcinyl triazine type; benzotriazole derivatives; benzalmalonate derivatives; benzimidazole derivatives; imidazolines; bis-benzazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303,549, DE-197,26,184 and EP-893,119; benzoxazole derivatives such as those described in EP-0,832,642; EP-2,027,883, EP-1,300,137 and DE-101,62,844; screening polymers and screening silicones such as those described especially in WO 93/04665; dimers derived from α-alkylstyrene, such as those described in DE-198,55,649; 4,4-diarylbutadienes such as those described in EP-0,967,200, DE-197,46,654, DE-197,55,649, EP-A-1,008,586, EP-1,133,980 and EP-133,981, and mixtures thereof.

As examples of additional organic photoprotective agents, mention may be made of those denoted hereinbelow under their INCI name:

para-Aminobenzoic Acid Derivatives:
PABA,
Ethyl PABA,
Ethyl dihydroxypropyl PABA,
Ethylhexyl dimethyl PABA marketed in particular under the name "Escalol 507" by ISP,
Glyceryl PABA,
PEG-25 PABA marketed under the name "Uvinul P25" by BASF.

Salicylic Derivatives:
Homosalate marketed under the name "Eusolex HMS" by Rona/EM Industries,
Ethylhexyl salicylate marketed under the name "Neo Heliopan OS" by Haarmann and Reimer,
Dipropylene glycol salicylate marketed under the name "Dipsal" by Scher,
TEA salicylate marketed under the name "Neo Heliopan TS" by Haarmann and Reimer.

β,β-Diphenylacrylate Derivatives:
Octocrylene marketed in particular under the trademark "Uvinul N539" by BASF,
Etocrylene marketed in particular under the trademark "Uvinul N35" by BASF.

Benzophenone Derivatives:
Benzophenone-1 marketed under the trademark "Uvinul 400" by BASF,
Benzophenone-2 marketed under the trademark "Uvinul D50" by BASF,
Benzophenone-3 or Oxybenzone marketed under the trademark "Uvinul M40" by BASF,
Benzophenone-4 marketed under the trademark "Uvinul MS40" by BASF,
Benzophenone-5,
Benzophenone-6 marketed under the trademark "Helisorb 11" by Norquay,
Benzophenone-8 marketed under the trademark "Spectra-Sorb UV-24" by American Cyanamid,
Benzophenone-9 marketed under the trademark "Uvinul DS-49" by BASF,
Benzophenone-12
n-hexyl 2-(4-diethylamino-2-hydroxybenzoyl)benzoate.

Benzylidenecamphor Derivatives:
3-Benzylidenecamphor manufactured under the name "Mexoryl SD" by Chimex,
4-Methylbenzylidenecamphor marketed under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.

Phenylbenzimidazole Derivatives:
Phenylbenzimidazolesulfonic acid marketed in particular under the trademark "Eusolex 232" by Merck,
Disodium phenyl dibenzimidazole tetrasulfonate marketed under the trademark "Neo Heliopan AP" by Haarmann and Reimer.

Phenylbenzotriazole Derivatives:
Drometrizole trisiloxane marketed under the name "Silatrizole" by Rhodia Chimie, Methylenebis(benzotriazolyl)tetramethylbutylphenol marketed in solid form under the trademark "MIXXIM BB/100" by Fairmount Chemical, or in micronized form as an aqueous dispersion under the trademark "Tinosorb M" by Ciba Specialty Chemicals.

Triazine Derivatives:

Ethylhexyltriazone marketed in particular under the trademark "Uvinul T150" by BASF, Diethylhexylbutamidotriazone marketed under the trademark "Uvasorb HEB" by Sigma 3V, 2,4,6-tris(diisobutyl 4'-aminobenzalmalonate)-s-triazine.

Anthranilic Derivatives:

Menthyl anthranilate marketed under the trademark "Neo Heliopan MA" by Haarmann and Reimer.

Imidazoline Derivatives:

Ethylhexyldimethoxybenzylidenedioxoimidazoline propionate.

Benzalmalonate Derivatives:

Polyorganosiloxane containing benzalmalonate functions, for instance Polysilicone-15, marketed under the trademark "Parsol SLX" by Hoffmann LaRoche 4,4-Diarylbutadiene Derivatives:

1,1-Dicarboxy(2,2'-dimethylpropyl)-4,4-diphenylbutadiene

Benzoxazole Derivatives:

2,4-bis[5-(1-dimethylpropyl)benzoxazol-2-yl(4-phenyl)imino]-6-(2-ethylhexyl)imino-1,3,5-triazine marketed under the name Uvasorb K2A by Sigma 3V and mixtures thereof.

The preferred additional organic photoprotective agents are selected from among:

Homosalate,
Ethylhexyl salicylate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Ethylhexyl Triazone,
Diethylhexyl Butamido Triazone,
Drometrizole trisiloxane,
Polysilicone-15,
1,1-Dicarboxy(2,2'-dimethylpropyl)4,4-diphenylbutadiene,
2,4-Bis[5-1(dimethylpropyl)benzoxazol-2-yl(4-phenyl)imino]-6-(2-ethylhexyl)imino-1,3,5-triazine,
and mixtures thereof.

The additional mineral photoprotective agents are selected from among pigments and even more preferably nanopigments (mean size of the primary particles: generally from 5 nm to 100 nm and preferably from 10 nm to 50 nm) of treated or untreated metal oxides such as, for example, nanopigments of titanium oxide (amorphous or crystallized in rutile and/or anatase form), of iron oxide, of zinc oxide, of zirconium oxide or of cerium oxide.

The treated nanopigments are pigments that have undergone one or more surface treatments of chemical, electronic, mechanochemical and/or mechanical nature with compounds as described, for example, in *Cosmetics & Toiletries*, February 1990, Vol. 105, pp. 53-64, such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen or elastin), alkanolamines, silicon oxides, metal oxides, sodium hexametaphosphate, alumina or glycerol.

The treated nanopigments may more particularly be titanium oxides treated with:

silica and alumina, such as the products "Microtitanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide, alumina and aluminum stearate, such as the product "Microtitanium Dioxide MT 100 T" from the company Tayca, alumina and aluminum laurate, such as the product "Microtitanium Dioxide MT 100 S" from the company Tayca, iron oxides and iron stearate, such as the product "Microtitanium Dioxide MT 100 F" from the company Tayca, silica, alumina and silicone, such as the products "Microtitanium Dioxide MT 100 SAS", "Microtitanium Dioxide MT 600 SAS" and "Microtitanium Dioxide MT 500 SAS" from the company Tayca, sodium hexametaphosphate, such as the product "Microtitanium Dioxide MT 150 W" from the company Tayca, octyltrimethoxysilane, such as the product "T-805" from the company Degussa, alumina and stearic acid, such as the product "UVT-M160" from the company Kemira, alumina and glycerol, such as the product "UVT-M212" from the company Kemira, alumina and silicone, such as the product "UVT-M262" from the company Kemira.

Other titanium oxide nanopigments treated with a silicone are preferably $TiO_2$ treated with octyltrimethylsilane and for which the mean size of the elementary particles is from 25 to 40 nm, such as the product marketed under the trademark "T805" by Degussa Silices, $TiO_2$ treated with a polydimethylsiloxane and for which the mean size of the elementary particles is 21 nm, such as the product marketed under the trademark "70250 Cardre UF TiO2SI3" by Cardre, anatase/rutile $TiO_2$ treated with a polydimethylhydrogenosiloxane and for which the mean size of the elementary particles is 25 nm, such as the product marketed under the trademark "Microtitanium Dioxide USP Grade Hydrophobic" by Color Techniques.

The uncoated titanium oxide nanopigments are marketed, for example, by Tayca under the trademarks "Microtitanium Dioxide MT 500 B" or "Microtitanium Dioxide MT 600 B", by Degussa under the name "P 25", by Wackher under the name "Oxyde de titane transparent PW", by Myoshi Kasei under the name "UFTR", by Tomen under the name "ITS" and by Tioxide under the name "Tioveil AQ".

The uncoated zinc oxide nanopigments are, for example:

those marketed under the name "Z-Cote" by Sunsmart;

those marketed under the name "Nanox" by Elementis;

those marketed under the name "Nanogard WCD 2025" by Nanophase Technologies.

The coated zinc oxide nanopigments are, for example:

those marketed under the name "Zinc Oxide CS-5" by Toshibi (ZnO coated with polymethylhydrogenosiloxane);

those marketed under the name "Nanogard Zinc Oxide FN" by Nanophase Technologies (as a 40% dispersion in Finsolv TN, $C_{12}$-$C_{15}$ alkyl benzoate);

those marketed under the name "Daitopersion ZN-30" and "Daitopersion ZN-50" by Daito (dispersions in cyclopolymethylsiloxane/oxyethylenated polydimethylsiloxane, containing 30% or 50% of nanozinc oxides coated with silica and polymethylhydrogenosiloxane);

those marketed under the name "NFD Ultrafine ZNO" by Daikin (ZnO coated with perfluoroalkyl phosphate and copolymer based on perfluoroalkylethyl as a dispersion in cyclopentasiloxane);

those marketed under the name "SPD-Z1" by Shin-Etsu (ZnO coated with silicone-grafted acrylic polymer, dispersed in cyclodimethylsiloxane);

those marketed under the name "Escalol Z100" by ISP (alumina-treated ZnO dispersed in an ethylhexyl methoxycinnamate/PVP-hexadecene/methicone copolymer mixture);

those marketed under the name "Fuji ZNO-SMS-10" by Fuji Pigment (ZnO coated with silica and polymethylsilsesquioxane);

those marketed under the name "Nanox Gel TN" by Elementis (ZnO dispersed at a concentration of 55% in $C_{12}$-$C_{15}$ alkyl benzoate with hydroxystearic acid polycondensate).

The uncoated cerium oxide nanopigments are marketed under the name "Colloidal Cerium Oxide" by Rhone-Poulenc.

The uncoated iron oxide nanopigments are marketed, for example, by Arnaud under the names "Nanogard WCD 2002 (FE 45B)", "Nanogard Iron FE 45 BL AQ", "Nanogard FE 45R AQ" and "Nanogard WCD 2006 (FE 45R)" or by Mitsubishi under the name "TY-220", The coated iron oxide nanopigments are marketed, for example, by Arnaud under the names "Nanogard WCD 2008 (FE 45B FN)", "Nanogard WCD 2009 (FE 45B 556)", "Nanogard FE 45 BL 345" and "Nanogard FE 45 BL" or by BASF under the name "Transparent Iron Oxide".

Mention may also be made of mixtures of metal oxides, especially of titanium dioxide and of cerium dioxide, including the silica-coated equal-weight mixture of titanium dioxide and of cerium dioxide, marketed by Ikeda under the name "Sunveil A", and also the alumina, silica and silicone-coated mixture of titanium dioxide and of zinc dioxide, such as the product "M 261" marketed by Kemira, or the alumina, silica and glycerol-coated mixture of titanium dioxide and of zinc dioxide, such as the product "M 211" marketed by Kemira.

The nanopigments may be introduced into the compositions according to the invention in unmodified form or in the form of pigmentary paste, i.e., as a mixture with a dispersant, as described, for example, in GB-A-2,206,339.

The additional photoprotective agents are generally present in the compositions according to the invention in proportions ranging from 0.01% to 20% by weight relative to the total weight of the composition and preferably ranging from 0.1% to 10% by weight relative to the total weight of the composition.

The compositions according to the invention may also contain agents for artificially tanning and/or browning the skin (self-tanning agents) and more particularly dihydroxyacetone (DHA). They are preferably present in amounts ranging from 0.1% to 10% by weight relative to the total weight of the composition.

The compositions in accordance with the present invention may also comprise standard cosmetic adjuvants selected especially from fatty substances, organic solvents, ionic or nonionic, hydrophilic or lipophilic thickeners, softeners, humectants, opacifiers, stabilizers, emollients, silicones, antifoams, fragrances, preservatives, anionic, cationic, nonionic, zwitterionic or amphoteric surfactants, active agents, fillers, polymers, propellants, acidifying or basifying agents or any other ingredient usually used in cosmetics and/or dermatology.

The fatty substances may consist of an oil or a wax or mixtures thereof. The term "oil" means a compound that is liquid at room temperature. The term "wax" means a compound that is solid or substantially solid at room temperature and whose melting point is generally greater than 35° C.

Oils that may be mentioned include mineral oils (paraffin); plant oils (sweet almond oil, macadamia oil, grapeseed oil or jojoba oil); synthetic oils, for instance perhydrosqualene, fatty alcohols, fatty acids or fatty esters (for instance the $C_{12}$-$C_{15}$ alkyl benzoate marketed under the trademark "Finsolv TN" by Witco, octyl palmitate, isopropyl lanolate and triglycerides, including capric/caprylic acid triglycerides), oxyethylenated or oxypropylenated fatty esters and ethers; silicone oils (cyclomethicone and polydimethylsiloxanes, or PDMS) or fluoro oils, and polyalkylenes.

Waxy compounds that may be mentioned include paraffin, carnauba wax, beeswax and hydrogenated castor oil.

Among the organic solvents that may be mentioned are lower alcohols and polyols. These polyols may be selected from glycols and glycol ethers, for instance ethylene glycol, propylene glycol, butylene glycol, dipropylene glycol or diethylene glycol.

Hydrophilic thickeners that may be mentioned include carboxyvinyl polymers such as the Carbopol products (carbomers) and the Pemulen products (acrylate C10-C30-alkylacrylate copolymer); polyacrylamides, for instance the crosslinked copolymers marketed under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methylpropanesulfonic acid) marketed by Hoechst under the trademark "Hostacerin AMPS" (CTFA name: ammonium polyacryldimethyltauramide); cellulose-based derivatives such as hydroxyethylcellulose; polysaccharides and especially gums such as xanthan gum; and mixtures thereof.

Lipophilic thickeners that may be mentioned include modified clays such as hectorite and its derivatives, for instance the products marketed under the name bentone.

Among the active agents that may be mentioned are:
antipollution agents and/or free-radical scavengers;
depigmenting agents and/or propigmenting agents;
antiglycation agents;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
tensioning agents;
desquamating agents;
moisturizers;
anti-inflammatory agents;
agents acting on the energy metabolism of cells;
insect repellants;
substance P or CGRP antagonists.

Needless to say, one skilled in this art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention may be prepared according to techniques that are well known to those skilled in the art, in particular those intended for the preparation of emulsions of oil-in-water or water-in-oil type. They may be in particular in the form of a simple or complex emulsion (O/W, W/O, O/W/O or W/O/W emulsion) such as a cream or a milk, in the form of a gel or a cream-gel, or in the form of a lotion, a powder or a solid tube, and may optionally be packaged as an aerosol and may be in the form of a mousse or a spray.

The compositions according to the invention are preferably in the form of an oil-in-water or water-in-oil emulsion.

The emulsions generally contain at least one emulsifier selected from amphoteric, anionic, cationic and nonionic emulsifiers, which are used alone or as a mixture. The emulsifiers are appropriately selected according to the emulsion to be obtained (W/O or O/W).

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, marketed under the name "DC 5225 C" by Dow Corning, and alkyldimethicone copolyols such as laurylmethicone copolyol marketed under the name "Dow Corning 5200 Formulation Aid" by Dow Corning; cetyldimethicone copolyol, such as the product marketed under the name Abil EM 90R by Goldschmidt, and the mixture of cetyldimethicone copolyol, of polyglyceryl isostearate (4 mol) and of hexyl laurate, marketed under the name Abil WE O9 by Goldschmidt. One or more co-emulsifiers may also be added thereto, which may be selected advantageously from the group comprising polyol alkyl esters. Polyol alkyl esters that may especially be mentioned include glycerol and/or sorbitan esters, for example polyglyceryl isostearate, such as the product marketed under the name Isolan GI 34 by Goldschmidt, sorbitan isostearate, such as the product marketed under the name Arlacel 987 by ICI, sorbitan glyceryl isostearate, such as the product marketed under the name Arlacel 986 by ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside marketed, for example, by Henkel under the respective names Plantaren 2000 and Plantaren 1200, cetostearyl glucoside optionally as a mixture with cetostearyl alcohol, marketed, for example, under the name Montanov 68 by SEPPIC, under the name Tegocare CG90 by Goldschmidt and under the name Emulgade KE3302 by Henkel, and also arachidyl glucoside, for example in the form of a mixture of arachidyl alcohol, behenyl alcohol and arachidyl glucoside, marketed under the name Montanov 202 by SEPPIC. According to one particular embodiment of the invention, the mixture of the alkylpolyglucoside as defined above with the corresponding fatty alcohol may be in the form of a self-emulsifying composition as described, for example, in WO-A-92/06778.

When it is an emulsion, the aqueous phase of this emulsion may comprise a nonionic vesicular dispersion prepared according to known processes (Bangham, Standish and Watkins, *J. Mol. Biol.*, 13, 238 (1965), FR-2,315,991 and FR-2,416,008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

The present invention also features the use of the compositions according to the invention as defined above for the manufacture of cosmetic products for treating the skin, the lips, the nails, the hair, the eyelashes, the eyebrows and/or the scalp, especially care products and makeup products.

The cosmetic compositions according to the invention may be used, for example, as care products and/or antisun products for the face and/or the body, of liquid to semi-liquid consistency, such as milks, more or less rich creams, cream-gels and pastes. They may optionally be packaged as an aerosol and may be in the form of mousses or sprays.

The compositions according to the invention in the form of vaporizable fluid lotions in accordance with the invention are applied to the skin or the hair in the form of fine particles by means of pressurization devices. The devices in accordance with the invention are well known to those skilled in the art and include non-aerosol pumps or "atomizers", aerosol containers comprising a propellant and also aerosol pumps using compressed air as propellant. The latter pumps are described in U.S. Pat. Nos. 4,077,441 and 4,850,517 (forming an integral part of the content of the description).

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

The following specific antisun/sunscreen formulations were prepared; the amounts are indicated in percentages by weight:

Compositions Example 1

| PHASE A: | |
|---|---|
| Polydimethylsiloxane | 0.5 |
| Preservatives | 1.0 |
| Stearic acid | 1.5 |
| Glyceryl monostearate/PEG stearate mixture (100 EO) | 1.0 |
| Cetylstearyl glucoside/cetylstearyl alcohol mixture | 2.0 |
| Cetyl alcohol | 0.5 |
| Butylmethoxydibenzoylmethane | 2.0 |
| 2-Phenylethyl benzoate (X-Tend 226 from ISP) | 15 |
| Bis(ethylhexyloxyphenol)methoxyphenyltriazine (Tinosorb S from Ciba Geigy) | 5 |

-continued

| PHASE B: | |
|---|---|
| Deionized water | qs 100 |
| Sequestering agent | 0.1 |
| Glycerol | 5.0 |
| Xanthan gum | 0.2 |
| Monocetyl phosphate | 1.0 |
| PHASE C: | |
| Isohexadecane | 1.0 |
| Acrylic acid/stearyl methacrylate copolymer | 0.2 |
| Triethanolamine | qs |

The aqueous phase (Phase B) containing all of its ingredients is heated to 80° C. on a water bath. The fatty phase (Phase A) containing all of its ingredients is heated to 80° C. on a water bath. A is emulsified in B with stirring of rotor-stator type (machine from the company Moritz). Phase C is incorporated and the mixture is allowed to cool to room temperature with moderate stirring. The triethanolamine is introduced so as to adjust the pH to the desired value at the end of manufacture.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, photostable cosmetic/dermatological photoprotective composition, comprising an effective UV-photoprotecting amount of at least one dibenzoylmethane UV-screening agent, and, as a stabilizing admixture therefor, a thus effective amount of at least one arylalkyl benzoate compound and at least one bis-resorcinyl triazine compound, formulated into a topically applicable, cosmetically/dermatologically acceptable medium.

2. The cosmetic/dermatological composition as defined by claim 1, said at least one dibenzoylmethane UV-screening agent being selected from the group consisting of:
   2-methyldibenzoylmethane;
   4-methyldibenzoylmethane;
   4-isopropyldibenzoylmethane;
   4-tert-butyldibenzoylmethane;
   2,4-dimethyldibenzoylmethane;
   2,5-dimethyldibenzoylmethane;
   4,4'-diisopropyldibenzoylmethane;
   4,4'-dimethoxydibenzoylmethane;
   4-tert-butyl-4'-methoxydibenzoylmethane;
   2-methyl-5-isopropyl-4'-methoxydibenzoylmethane;
   2-methyl-5-tert-butyl-4'-methoxydibenzoylmethane;
   2,4-dimethyl-4'-methoxydibenzoylmethane; and
   2,6-dimethyl-4-tert-butyl-4'-methoxydibenzoylmethane.

3. The cosmetic/dermatological composition as defined by claim 1, said at least one dibenzoylmethane UV-screening agent comprising 4-(tert-butyl)-4'-methoxydibenzoylmethane or Butyl Methoxy Dibenzoylmethane.

4. The cosmetic/dermatological composition as defined by claim 1, said at least one arylalkyl benzoate compound having the formula (I) or (II) below:

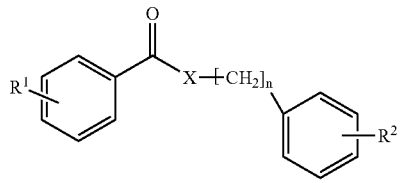

(I)

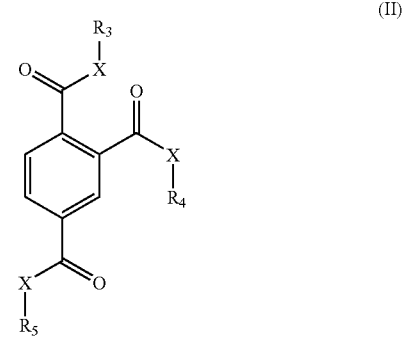

(II)

in which:
   X is O, S or N;
   n is an integer ranging from 1 to 10;
   $R^1$ and $R^2$, which may be identical or different, are each a hydrogen atom, a hydroxyl group, a linear or branched $C_1$-$C_4$ alkoxy radical, a nitro radical, an amino radical, or a $C_6H_6SO_2$ radical;
   $R^3$, $R^4$ and $R^5$, which may be identical or different, are each a radical of formula:

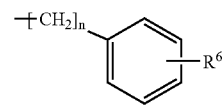

in which n has the same definition indicated above; and $R^6$ is a hydrogen atom, a hydroxyl group, a linear or branched $C_1$-$C_4$ alkoxy radical, a nitro radical, an amino radical, or a $C_6H_6SO_2$ radical.

5. The cosmetic/dermatological composition as defined by claim 4, said at least one arylalkyl benzoate compound comprising 2-phenylethyl benzoate of formula:

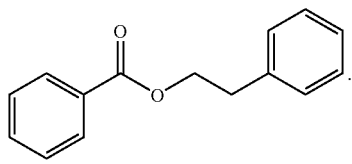

6. The cosmetic/dermatological composition as defined by claim 1, said at least one bis-resorcinyl triazine compound having the formula (II) below:

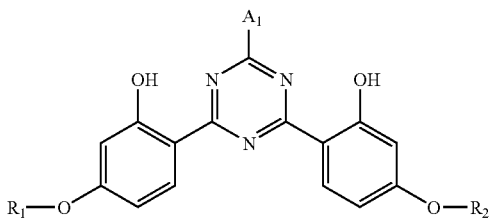

(III)

in which:

(i) the radicals $R_1$ and $R_2$, which may be identical or different, are each a $C_3$-$C_8$ alkyl radical, a $C_2$-$C_{18}$ alkenyl radical or a residue of formula —$CH_2$—$CH$(OH)—$CH_2$—$OT_1$ in which $T_1$ is a hydrogen atom or a $C_1$-$C_8$ alkyl radical;

(ii) the radicals $R_1$ and $R_2$, which may be identical or different, are each a residue of formula (1) below:

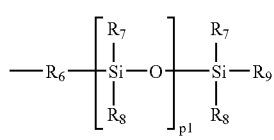

(1)

in which:

$R_6$ is a covalent bond, a linear or branched $C_1$-$C_4$ alkyl radical or a residue of formula —$C_{m1}H_{2m1}$—O— in which m1 is a number ranging from 1 to 4;

p1 is a number ranging from 0 to 5;

the radicals $R_7$, $R_8$ and $R_9$, which may be identical or different, are each a $C_1$-$C_{18}$ alkyl radical, a $C_1$-$C_{18}$ alkoxy radical or a residue of formula:

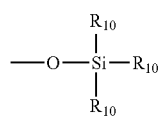

(2)

in which $R_{10}$ is a $C_1$-$C_5$ alkyl radical;

$A_1$ is a radical having one of the following formulae:

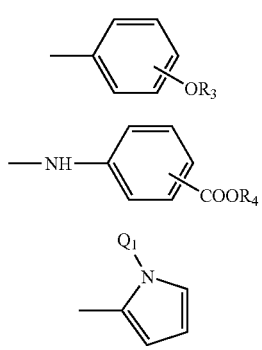

(3)

(4)

(5)

in which:

$R_3$ is a hydrogen atom, a $C_1$-$C_{10}$ alkyl radical, a radical of formula: —$(CH_2CHR_5$—O$)_{n1}R_4$ in which n1 is a number ranging from 1 to 16 or a residue of structure $CH_2$—$CH$—(OH)—$CH_2OT_1$ with $T_1$ having the same definition indicated above;

$R_4$ is hydrogen, a metallic cation M, a $C_1$-$C_5$ alkyl radical or a residue of formula —$(CH_2)m_2$-$OT_1$ in which $m_2$ is a number ranging from 1 to 4 and $T_1$ has the same definition indicated above; and $Q_1$ is a $C_1$-$C_{18}$ alkyl radical.

7. The cosmetic/dermatological composition as defined by claim 6, said at least one bis-resorcinyl triazine compound of formula (III) being selected from the group consisting of:

2,4-bis{[4-(2-ethylhexyloxy)-2-hydroxy]phenyl}-6-(4-methoxyphenyl)-1,3,5-triazine;

2,4-bis{[4-(3-(2-propyloxy)-2-hydroxypropyloxy)-2-hydroxy]phenyl}-6-(4-methoxyphenyl)-1,3,5-triazine;

2,4-bis{[4-(2-ethylhexyloxy)-2-hydroxy]phenyl}-6-[4-(2-methoxyethylcarboxyl)phenylamino]-1,3,5-triazine;

2,4-bis{[4-tris(trimethylsiloxysilylpropyloxy)-2-hydroxy]phenyl}-6-(4-methoxyphenyl)-1,3,5-triazine;

2,4-bis{[4-(2"-methylpropenyloxy)-2-hydroxy]phenyl}-6-(4-methoxyphenyl)-1,3,5-triazine;

2,4-bis{[4(1',1',1',3',5',5',5'-heptamethyltrisiloxy-2"-methylpropyloxy)-2-hydroxy]phenyl}-6-(4-methoxyphenyl)-1,3,5-triazine;

2,4-bis{[4-(3-(2-propyloxy)-2-hydroxypropyloxy)-2-hydroxy]phenyl}-6-[(4-ethylcarboxyl)phenylamino]-1,3,5-triazine; and 2,4-bis{[4-(2-ethylhexyloxy)-2-hydroxy]phenyl}-6-(1-methylpyrrol-2-yl)-1,3,5-triazine.

8. The cosmetic/dermatological composition as defined by claim 7, said at least one bis-resorcinyl triazine compound of formula (II) comprising 2,4-bis{[4-(2-ethylhexyloxy)-2-hydroxy]phenyl}-6-(4-methoxyphenyl)-1,3,5-triazine (Bis-Ethylhexyloxyphenol Methoxyphenyl Triazine).

9. The cosmetic/dermatological composition as defined by claim 1, said at least one dibenzoylmethane UV-screening agent comprising from 0.01% to 10% by weight thereof.

10. The cosmetic/dermatological composition as defined by claim 1, said at least one bis-resorcinyl triazine compound comprising from 0.1% to 20% by weight thereof.

11. The cosmetic/dermatological composition as defined by claim 1, further comprising at least one other UV-A-active and/or UV-B-active organic or mineral photoprotective agent that is water-soluble or liposoluble or insoluble in the cosmetic solvents commonly employed.

12. The cosmetic/dermatological composition as defined by claim 11, comprising at least one additional organic photoprotective agent selected from among cinnamic derivatives, anthranilates; salicylic derivatives, camphor derivatives; triazine derivatives other than those of the bis-resorcinyl triazine type; benzophenone derivatives; β,β-diphenylacrylate derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; α-alkylstyrene derivatives, 4,4-diarylbutadienes, and mixtures thereof.

13. The cosmetic/dermatological composition as defined by claim 12, comprising at least one additional organic UV-screening agent selected from among the following compounds:

Homosalate,

Ethylhexyl salicylate,

Octocrylene,

Phenylbenzimidazolesulfonic acid,

Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Ethylhexyl Triazone,
Diethylhexyl Butamido Triazone,
Drometrizole trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine,
and mixtures thereof.

14. The cosmetic/dermatological composition as defined by claim 11, comprising at least one additional mineral photoprotective agent which comprises treated or untreated metal oxide pigments or nanopigments.

15. The cosmetic/dermatological composition as defined by claim 14, comprising pigments or nanopigments selected from among titanium oxide, zinc oxide, iron oxide, zirconium oxide and cerium oxide, and mixtures thereof, which are treated or untreated.

16. The cosmetic/dermatological composition as defined by claim 1, further comprising at least one agent for artificially tanning and/or browning the skin.

17. The cosmetic/dermatological composition as defined by claim 1, further comprising at least one adjuvant selected from among fatty substances, organic solvents, ionic or nonionic, hydrophilic or lipophilic thickeners, softeners, humectants, opacifiers, stabilizers, emollients, silicones, antifoams, fragrances, preservatives, anionic, cationic, nonionic, zwitterionic or amphoteric surfactants, active agents, fillers, polymers, propellants and acidifying or basifying agents.

18. A regime or regimen for cosmetically treating or caring for the skin, lips, nails, hair, eyelashes, eyebrows and/or scalp of an individual in need of such treatment, comprising topically applying thereon, a thus effective amount of the cosmetic/dermatological composition as defined by claim 1.

19. A regime or regimen for photoprotecting the skin, hair, lips and/or scalp against the damaging effects of UV-irradiation, comprising topically applying thereon, a thus effective amount of the cosmetic/dermatological composition as defined by claim 1.

20. A process for enhancing the stability with respect to UV-irradiation of at least one dibenzoylmethane UV-screening agent, comprising formulating therewith a thus effective amount of at least one arylalkyl benzoate compound and at least one bis-resorcinyl triazine compound.

21. The cosmetic/dermatological composition as defined by claim 1, formulated as an emulsion, a milk, a gel, a cream, a lotion, a powder, a stick, a mousse, or a spray.

* * * * *